US00PP35020P2

(12) United States Plant Patent
Petter et al.

(10) Patent No.: US PP35,020 P2
(45) Date of Patent: Mar. 7, 2023

(54) SHALLOT PLANT NAMED 'INNOVATOR'

(50) Latin Name: *Allium cepa*
Varietal Denomination: Innovator

(71) Applicants: Bejo Zaden BV, Warmenhuizen (NL); De Groot en Slot BV, Broek op Langedijk (NL)

(72) Inventors: Timo Christiaan Petter, Warmenhuizen (NL); Lennaert Crispijn Aardse, Broek op Langedijk (NL)

(73) Assignees: De Groot en Slot B.V.; Bejo Zaden B.V.

( * ) Notice: Subject to any disclaimer, the term of this patent is extended or adjusted under 35 U.S.C. 154(b) by 0 days.

(21) Appl. No.: 17/300,896

(22) Filed: Dec. 9, 2021

(51) Int. Cl.
*A01H 5/04* (2018.01)
*A01H 6/04* (2018.01)

(52) U.S. Cl.
USPC ..... Plt./263.1
CPC ..... *A01H 6/045* (2018.05)

(58) Field of Classification Search
USPC ..... Plt./263.1, 258
CPC ..... A01H 6/045
See application file for complete search history.

(56) References Cited

PUBLICATIONS

CPVO hit on UPOV QZ PBR 2019/3287 on a shallot plant named, 'Innovator', filed Jan. 8, 2020.*
Bejo, "After years of breeding, Bejo/DGS introduces the first downy mildew resistant shallot from seed, Innovator", https://www.bejoseeds.com/magazine/bejo-and-de-groot-en-slot-launch-first-downy-mildew-resistant-shallot-seed, (c)2018.*
Bejo, Contact page, https:..www.bejoseeds.com/contact, (c)2018.*
UPOV hits on shallot plant named, 'Innovator', QZ PBR 20193287 filed Jan. 8, 2020, NL PBR SJL87 filed Jan. 16, 2019, and UK BGS124 filed Sep. 20, 2019, downloaded from www.pluto.upov.int on Dec. 9, 2022.*
CPVO hit on shallot plant named, 'Innovator', QZ PBR 20193287 filed Jan. 8, 2021.*

* cited by examiner

*Primary Examiner* — Anne Marie Grunberg
(74) *Attorney, Agent, or Firm* — The Webb Law Firm

(57) ABSTRACT

A new and distinct variety of shallot plant with high resistance to *Peronospora destructor* and long storability.

4 Drawing Sheets

Botanical classification: *Allium cepa.*
Varietal denomination: 'Innovator'.

BACKGROUND OF THE INVENTION

The present invention comprises a new and distinct shallot plant known by the varietal name 'Innovator'. The new variety is the result of a planned breeding program conducted in The Netherlands and was discovered in December of 2018. The purpose of the breeding program was to provide shallot varieties with harvest reliability, shape uniformity, and long storage life. 'Innovator' is the result of the crossing of an *Allium cepa* variety referred to by the applicant as 1010 (female parent, unpatented) with an *Allium cepa* variety referred to by the applicant as 1017 (male parent, unpatented). The claimed variety named 'Innovator' is one variety from the stated cross that was selected over its siblings for plant patent protection. The first act of asexual reproduction of 'Innovator' was conducted in April of 2021 by splitting and replanting its bulbs in soil in Broek op Langedijk, The Netherlands. 'Innovator' has been trial and field tested and has been found to retain its distinctive characteristics and remain true to type through successive asexual propagations. The present invention has not been evaluated under all possible environmental conditions. The phenotype may vary with variations in environment without a change in the genotype of the plant.

'Innovator' is similar to both of its parental varieties in time of harvest maturity and internal coloration. However, 'Innovator' exhibits a different shape and dry skin color than both of its parental varieties. Further, its female parent is distinguishable from 'Innovator' in being susceptible to mildew and shorter in overall plant length. Additionally, its male parent exhibits a longer overall plant length and darker overall coloration than 'Innovator'.

When compared to shallot variety named 'Conservor' (unpatented), 'Innovator' is similar to 'Conservor' in storage suitability. However, 'Innovator' exhibits a different dry skin color than 'Conservor' (RHS 176C for 'Innovator' and RHS 177C for 'Conservor'), a larger bulb size than 'Conservor', and a more elongated bulb shape than 'Conservor'). Further, contrary to 'Conservor', 'Innovator' is highly resistant to *Peronospora destructor.*

When compared to other shallot varieties known to the applicant, 'Innovator' can be distinguished based on its high resistance to *Peronospora destructor*, bulb size, shape, and dry skin color.

DESCRIPTION OF THE DRAWINGS

The accompanying photographic drawings illustrate the new variety, with the color being as nearly true as is possible with color illustrations of this type.

DESCRIPTION OF THE PLANT

Figure 1:
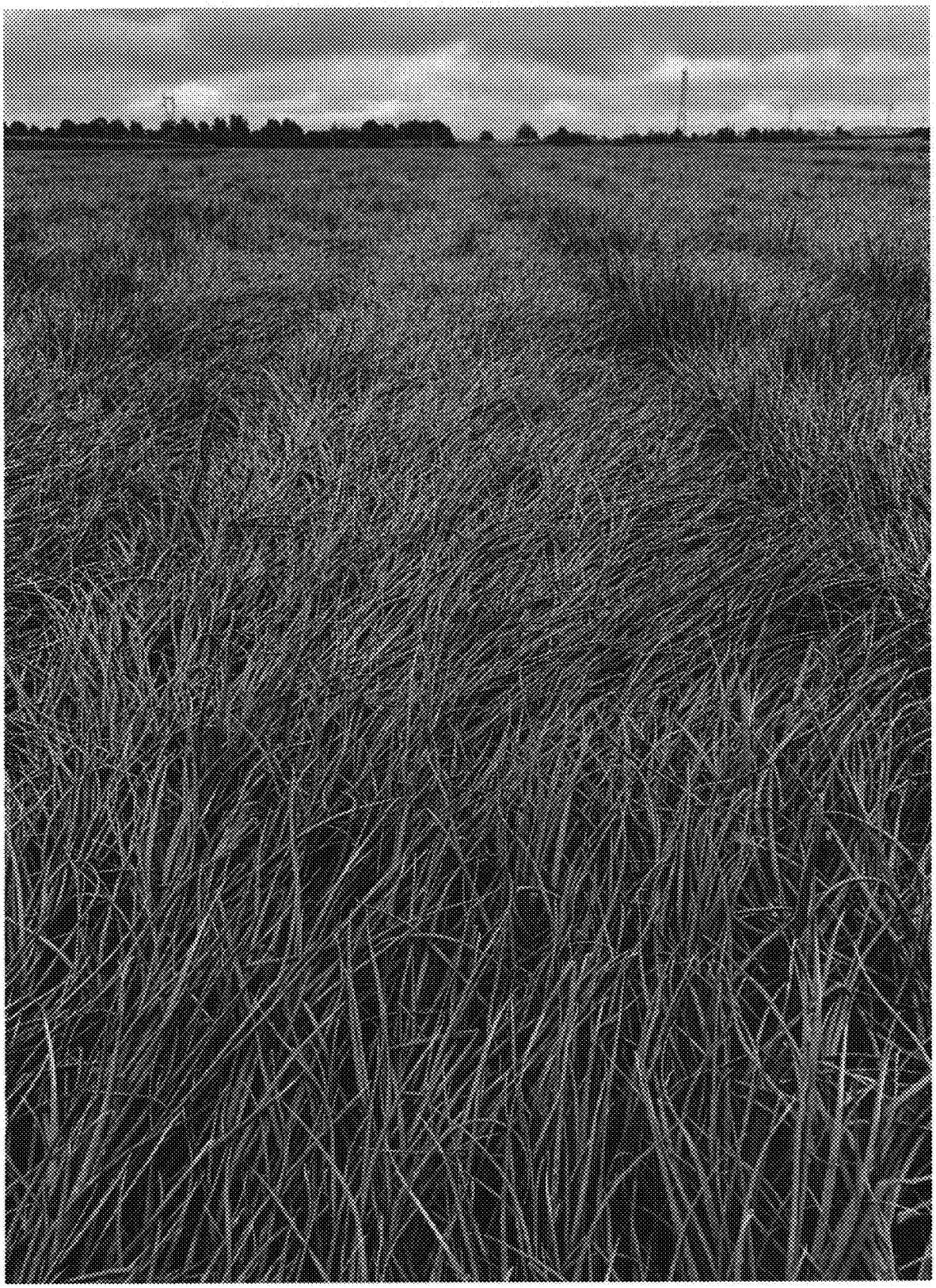
FIG. 1 shows a field of plants of the new variety (3 months after planting)
Figure 2:
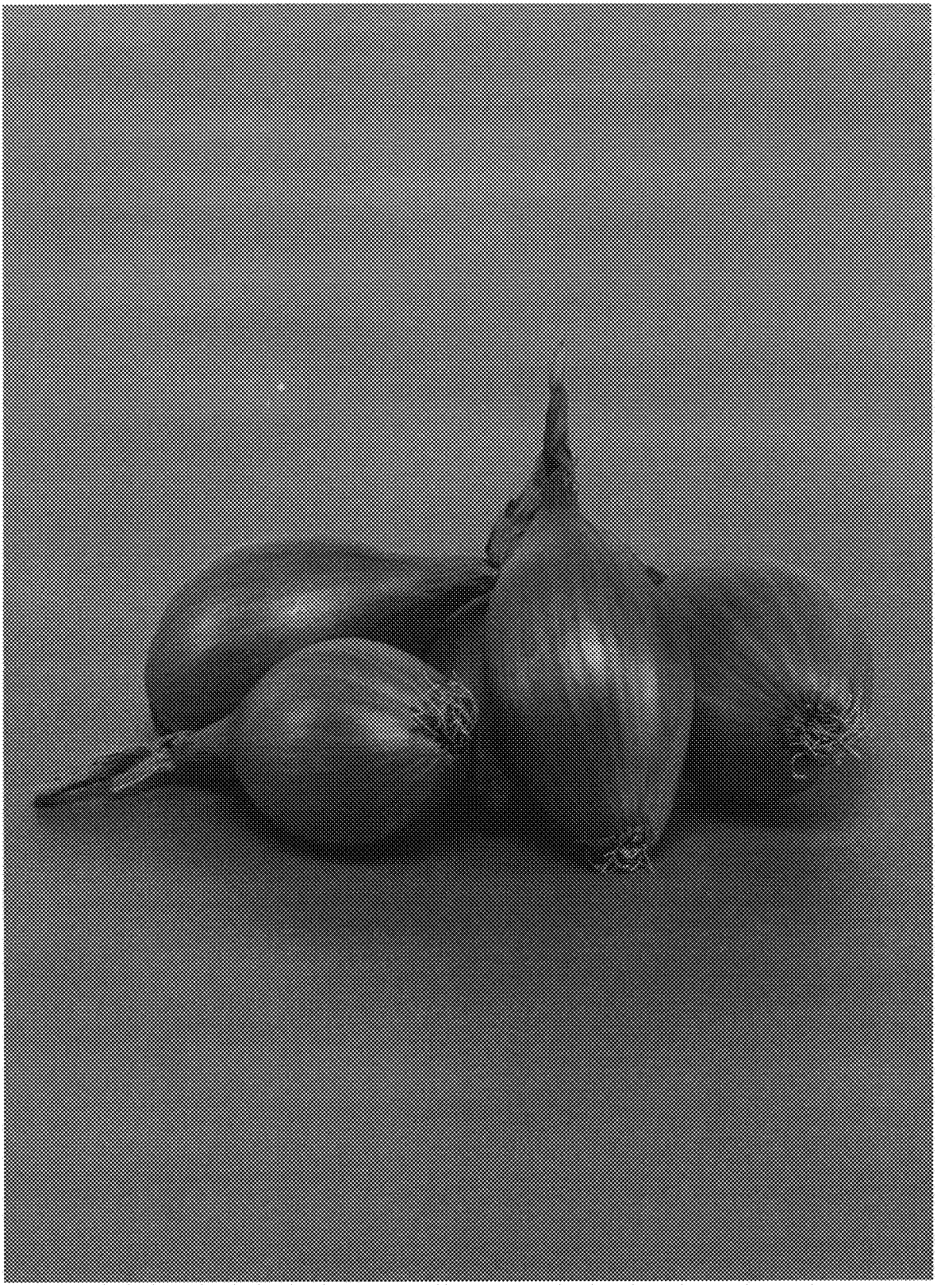
FIG. 2 shows multiple, dried bulbs of the new variety (3 months after harvest)
Figure 3:
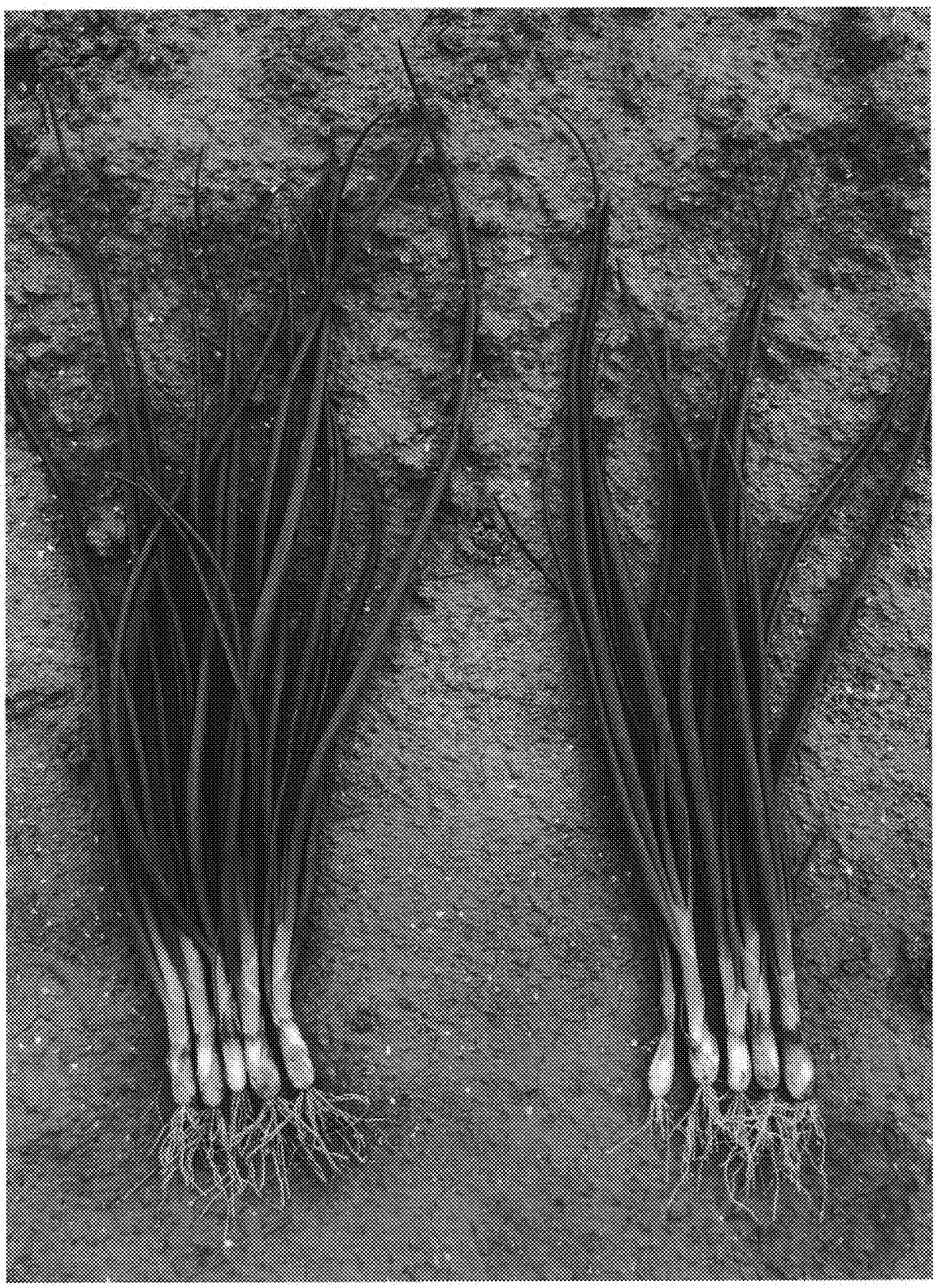
FIG. 3 shows multiple spears of the new variety (harvested 8 months after planting)
Figure 4:
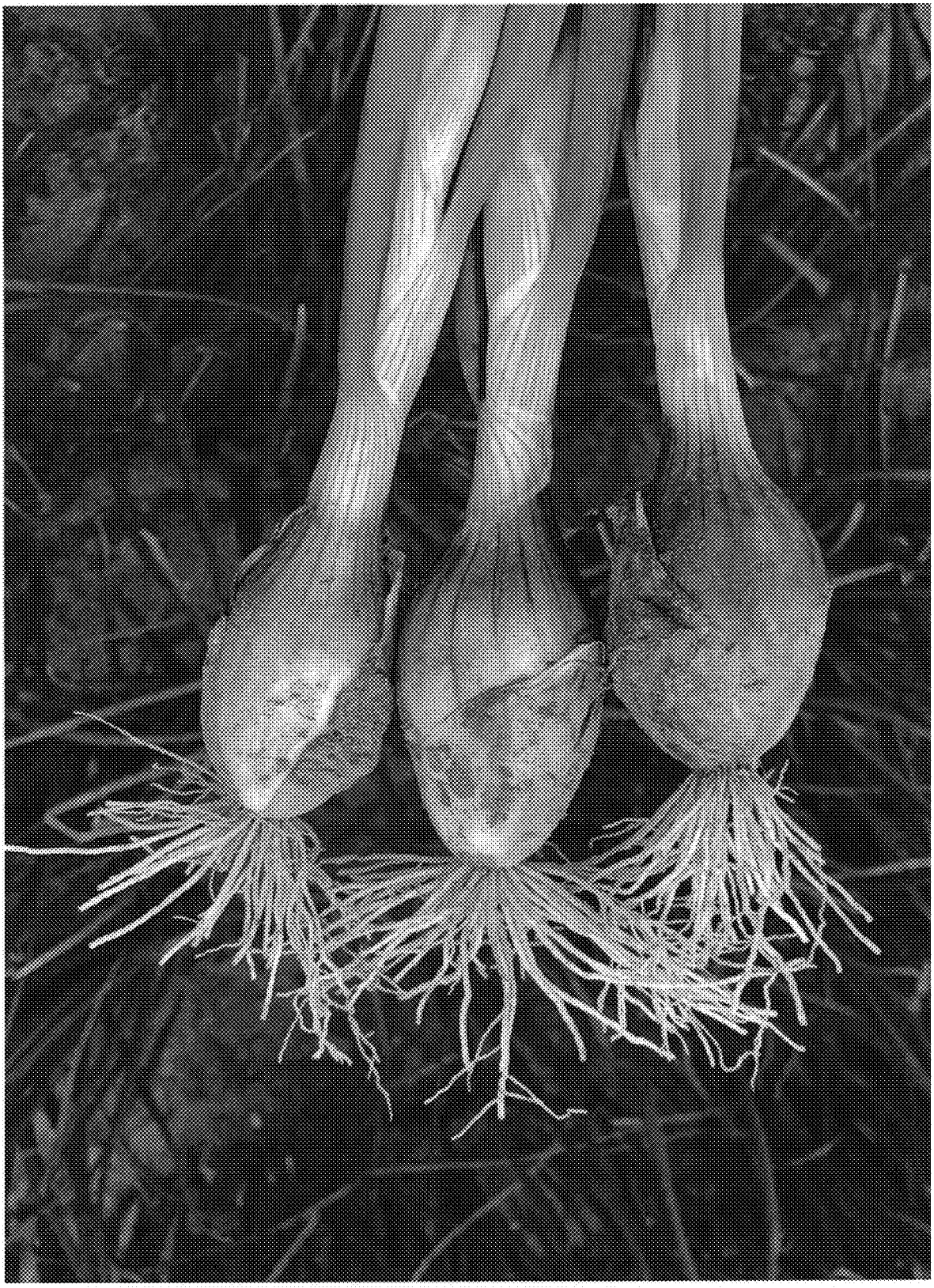
FIG. 4 shows a close-up view of freshly picked spears of the new variety (harvested 8 months after planting).

The following detailed description sets forth the characteristics of the new variety. Plants of the new variety were soil grown in the Netherlands under open field conditions under natural light. Growth conditions for 'Innovator' were maritime climatic conditions in a long-day region with more than 15 hours of daylight during the longest day. The new variety grows well in drained soil with a pH of about 5-7. Drilling or planting of bulbs can occur as early as the beginning of March, with harvest of bulbs at the end of August for Northern European conditions. Development of first leaves following planting/drilling is approximately 2-3 weeks. A planted bulb will mature in its first year and flower in its second year. The color readings and measurements were taken outdoors in the Netherlands under natural light on approximately 3 month old plants in the field and indoors under LED lights on 8 month old harvested plants. Color references are primarily to The 2019 R.H.S. Colour Chart of The Royal Horticultural Society of London, Sixth Edition.

PLANT

Bulb shape in longitudinal section: Elliptic.

*Height from soil line to top of bulb.*—Approximately 6-7 cm.

*Leaf length.*—Approximately 40-60 cm.

*Sheath height from soil line to base of lowest succulent leaf.*—Approximately 7-8 cm (before maturity yellowing begins).

*Hardiness.*—Bulb can be very firm up to 5 months after harvest.

*Rooting.*—Vigorous.

*Disease resistance.*—Highly resistant to *Peronospora destructor.*

*Tendency to bolt trials.*—Not suitable for Autumn sowing and Spring sown bolting tendency is very low — an approximate bolting time is not able to be provided.

Foliage:

*Attitude.*—Semi-erect.

*Waxiness.*—Thin and matte waxy layer present, having a color blend of RHS 189A and 189B.

*Cracking.*—None observed to date.

*Pseudostem length.*—9 cm.

*Pseudostem diameter.*—Approximately 1.2 cm.

*Pseudostem color.*—RHS NN155D with RHS 145A axial veins.

*Leaves.*—Number: Approximately 6-10 leaves per plant. Attachment and arrangement: Arranged on the disc-like pseudo stem in concentric circles. Length: Approximately 40-60 cm. Width: Approximately 1-2 cm. Aspect: Upright. Shape: Narrow. Apex: Pointed. Venation: Longitudinal, parallel veins present. Margin: Entire. Fragrance: Delicate, aromatic, and much sweeter than onion leaves. Texture: Smooth (both surfaces). Color: RHS 143A (both surfaces).

Bulbs:

*Height.*—Tall to very tall, approximately 6-7 cm.

*Width.*—Approximately 3-5 cm at widest point (the middle), with a neck of approximately 1.4 cm.

*Shape.*—Elliptic in longitudinal section, with a strongly tapered root end.

*Weight.*—Approximately 70 grams.

*Coloration of epidermis of fleshy scales.*—RHS 70B (immediately after harvest).

*Dried skin color* (3 *months after harvest*).—RHS 176C.

*Adherence of skin after harvest.*—Strong.

*Thickness of dried skin.*—Average.

*Flesh color.*—RHS 196D in the center, transitioning to RHS 70B toward the scales.

*Taste.*—Delicate and sweet with a hint of sharpness.

*Smell.*—Delicate, aromatic, and much sweeter than onions.

*Eating quality.*—Good and mild.

*Keeping quality.*—Suitable for long term storage.

*Number of growing points per Kg.*—Average to high.

*Bulblets.*—None observed.

Flowers:

*Inflorescence.*—Type: Umbel. Lastingness: 10 days. Size: 8.1 cm in depth and 8.1 cm in diameter. Fragrance: Faint and sweet. Number of flowers per inflorescence: Approximately 600.

*Bud.*—Length: 4 mm. Width: 3 mm. Shape: Ovate, triangular in cross section. Color: RHS 155C, with RHS 143B main veins of immature tepals.

*Form.*—Single.

*Length.*—1 cm.

*Width.*—1 cm.

*Tepals.*—Number: 6 per flower. Shape: Upper tepals: Oblong and slightly concave. Lower tepals: Ovate and slightly concave. Length: Upper tepals: Average of 5.5 mm. Lower tepals: Average of 4.0 mm. Width: Upper tepals: Average of 2.0 mm. Lower tepals: Average of 1.5 mm. Apex: Upper tepals: Abruptly acute. Lower tepals: Acute. Base: Broadly cuneate. Margin: Entire. Texture: Smooth and glabrous (both surfaces). Color: Fully opened, upper side: Upper and lower tepals are RHS N155A. Fully opened, under side: Upper tepals are RHS NN155D and lower tepals are RHS 155C.

*Stem* (*peduncle*).—Number per plant: 1. Shape: Elliptic. Length: Average of 131.3 cm. Diameter: Average of 2.1 cm at widest, flattened point and average of 1.7 cm at narrowest, flattened point. Surface: Smooth, glabrous, and covered with a very thin waxy layer. Color: RHS NN137B.

*Pedicel.*—Shape: Circular. Length: Average of 3.2 cm. Width: Average of 1 mm. Surface: Smooth, glabrous, moderately glossy. Color: RHS 138A and fading to RHS 144B towards the base.

Reproductive organs (100% male sterility):

*Gynoecium.*—Pistils: Number: Average of 1 per flower. Length: Average of 3.5 mm. Stigma: Width: Average of 0.2 mm. Color: RHS NN155D. Styles: Length: Average of 3 mm. Color: RHS NN155D. Ovary: Diameter: 3 mm. Color: RHS 157D, with RHS 143B veins.

*Androecium.*—Stamens: Number: Average of 6 per flower. Length: Average of 6 mm. Anthers: Length: Average of 1 mm. Color: RHS N148D. Pollen: Color: RHS 161D. Amount: Low. Filaments: Length: Average of 5 mm. Color: RHS NN155C.

*Fruit/seeds.*—None observed to date.

We claim:

1. A new and distinct variety of *Allium cepa* shallot plant, named 'Innovator', as is herein illustrated and described.

* * * * *